(12) United States Patent
Urbano

(10) Patent No.: US 9,345,613 B2
(45) Date of Patent: May 24, 2016

(54) REGULATABLE INTRAORAL MANDIBULAR ADVANCEMENT DEVICE, FOR PREVENTING SNORING AND SLEEP APNOEA

(75) Inventor: Jesus Garcia Urbano, Malaga (ES)

(73) Assignee: LABORATORIO ORTOPLUS, S.L., Malaga (ES)

(*) Notice: Subject to any disclaimer, the term of this patent is extended or adjusted under 35 U.S.C. 154(b) by 691 days.

(21) Appl. No.: 13/500,759

(22) PCT Filed: Jun. 2, 2010

(86) PCT No.: PCT/ES2010/070371
§ 371 (c)(1),
(2), (4) Date: Apr. 6, 2012

(87) PCT Pub. No.: WO2011/020936
PCT Pub. Date: Feb. 24, 2011

(65) Prior Publication Data
US 2012/0199136 A1    Aug. 9, 2012

(30) Foreign Application Priority Data
Oct. 22, 2009    (ES) .................................. 200902027

(51) Int. Cl.
*A61F 5/56*    (2006.01)
*A61F 5/37*    (2006.01)
(Continued)

(52) U.S. Cl.
CPC . *A61F 5/566* (2013.01); *A61B 5/00* (2013.01); *A61B 5/48* (2013.01); *A61B 5/4806* (2013.01);
(Continued)

(58) Field of Classification Search
CPC .............. A61C 7/00; A61C 7/06; A61C 7/08; A61C 7/36; A61F 5/00; A61F 5/56; A61F 5/566; A61B 5/00; A61B 5/48; A61B 5/4806; A61B 5/4818
USPC ................. 128/846, 848, 857, 859, 861–863, 128/205.25, 206.19, 206.24; 433/6, 7, 433/18–19, 37, 41, 140, 142, 146–147
See application file for complete search history.

(56) References Cited

U.S. PATENT DOCUMENTS 5,829,441 A * 11/1998 Kidd et al. ..................... 128/848
8,544,472 B2 * 10/2013 Gaskell .......................... 128/848
(Continued)

FOREIGN PATENT DOCUMENTS

DE        10341260        4/2005
DE     202008010330      10/2008
(Continued)

*Primary Examiner* — Alireza Nia
*Assistant Examiner* — Brandon L Jackson
(74) *Attorney, Agent, or Firm* — Sturm & Fix LLP

(57) ABSTRACT

The invention relates to a regulatable intraoral mandibular advancement device that can be used to prevent snoring and sleep apnoea. Said device comprises two splints connected by a central screw (1) inserted into a sheath (2) comprising an upper ring (3), said sheath being used as a guiding housing (4) for an upper bar (5) of an upper plate (6), and the lower part of the sheath comprising a longitudinal groove (8) enabling the course of an inner mobile threaded (10) ring (9) that is displaced by the screw (1), and on which a lower displacement ring (11) is arranged, open or closed, said ring being provided with a perpendicular hole (12) with elipsoidal conicity, in which the lower bar (13) fixed to the lower maxillary plate (14) is inserted. Said screw (1) is locked to the sheath (2) on its rear part.

13 Claims, 3 Drawing Sheets

(51) Int. Cl.
*A61C 5/14* (2006.01)
*A61F 11/00* (2006.01)
*A61B 19/00* (2006.01)
*A61C 3/00* (2006.01)
*A61C 9/00* (2006.01)
*A61C 5/00* (2006.01)
*A61C 3/06* (2006.01)
*A61B 5/00* (2006.01)
*A61C 7/36* (2006.01)
*A61C 7/00* (2006.01)
*A61C 7/08* (2006.01)
*A61F 5/00* (2006.01)
*A61C 7/06* (2006.01)
*A62B 7/10* (2006.01)
*A62B 18/02* (2006.01)
*A62B 18/08* (2006.01)

(52) U.S. Cl.
CPC ............... *A61B 5/4818* (2013.01); *A61C 7/00* (2013.01); *A61C 7/06* (2013.01); *A61C 7/08* (2013.01); *A61C 7/36* (2013.01); *A61F 5/00* (2013.01); *A61F 5/56* (2013.01)

(56) References Cited

U.S. PATENT DOCUMENTS

| | | | | |
|---|---|---|---|---|
| 2002/0151907 | A1* | 10/2002 | Day et al. | 606/130 |
| 2003/0217753 | A1 | 11/2003 | Thornton | |
| 2007/0235037 | A1 | 10/2007 | Thornton | |
| 2008/0135056 | A1* | 6/2008 | Nelissen | 128/848 |

FOREIGN PATENT DOCUMENTS

| | | |
|---|---|---|
| EP | 0599445 | 6/1994 |
| ES | 2110310 | 2/1998 |
| ES | 2118365 | 9/1998 |
| ES | 1056960 | 6/2004 |
| ES | 2311841 | 2/2009 |
| ES | 1069826 | 5/2009 |
| WO | 9809675 | 3/1998 |
| WO | 2006058514 | 6/2006 |

* cited by examiner

REGULATABLE INTRAORAL MANDIBULAR ADVANCEMENT DEVICE, FOR PREVENTING SNORING AND SLEEP APNOEA

CROSS REFERENCE TO RELATED APPLICATIONS

This application is a 371 of International Application No. PCT/ES/2010/070371, filed Jun. 2, 2010, claiming priority from Spanish Application No. ES P200902027, filed Oct. 22, 2009, and are incorporated by reference herein in their entirety.

OBJECTIVE OF THE INVENTION

The invention, as expressed by the title, relates to a regulatable intraoral mandibular advancement device for preventing snoring and sleep apnoea, which contributes to its intended function several advantages that will be specified later, apart from other advantages that are inherent to its organization and constitution, which imply all together an improved alternative to what is already known in the field.

More particularly, the objective of the invention focuses on a device whose purpose is to solve the problems caused by snoring and apnoea due to poor air flow through the pharynx, which is based essentially on causing a regulatable mandibular advancement, by which the mandible is forced to be progressively moved forward, thereby pulling the tongue and the tissues that block posturally the pharynx, said device comprising two splints connected by a screw, enabling the controlled millimetric movement of the lower splint, having the unique properties of allowing the opening of both jaws with a compensated mandibular advancement and an unrestricted mandibular movement the trajectory of which is guided by a central bar and bilateral tracks, that is to say, allowing the opening and lateral movements of the patients' mouth.

FIELD OF APPLICATION OF THE INVENTION

The invention is comprised in the technical field of odontology involved in the design and manufacturing of orthodontic devices, specifically in the field of intraoral, dental aparatology for the treatment of snoring and sleep apnoea.

BACKGROUND OF THE INVENTION

The treatment of snoring and sleep apnoea has taken on particular relevance in recent times. In the past years, more than 300 inventions have been registered in the US Patent and Trademark Office claiming a solution to the problem of snoring and sleep apnoea. The truth is that most of them are not delivering the intended result. Ineffective, and in many cases harmful, treatments are often promoted and advertised, leading to confusion for the patient.

Although much research has been done in recent years about snoring and apnoea, the details of which remain unclear, many factors have been identified that may lead to presentation of the disease, from the consideration of the alterations of the structure of the stomatognathic system that generate a muscle movement and the compensating behaviours, which may be maladaptive. In patent documents WO9809675, EP0599445, ES1056960U and US 2008/0135056 A1, among others, treatment procedures are proposed for sleep apnoea and snoring, which are devices/appliances that, in one way or another, can correct snoring and apnoea, but that do not allow any degree of freedom of mandibular movement for the user/patient. For example, the device that is subject of the registered patent US 2008/0135056 A1, consists of an element or screw bound to a bimaxilar splint proposing a mandibular position that is regulatable only in height.

For this, the present invention focuses on achieving the correction of apnoea and snoring by use of a device enabling an advanced position of the mandible with respect to the maxilla and that also provide the mandible of the user/patient with the possibility of lateral movements, opening of both jaws and a compensated advancement (guided by central bars).

The development, evolution and change of habits of the human species in the past centuries has seen the appearance of new diseases. Their very novelty implies that they are difficult to diagnose and sometimes difficult to cure.

The diet, the lack of physical exercise, obesity, stress, postural habits and a suite of other modern and neurological factors have lead to sleep disorders, snoring and the worsening of obstructive sleep apnoea, with decreases of human quality of life in more developed regions, resulting in states of drowsiness, anxiety and frequently impacting on the rate of work and traffic accidents.

The first objective of the proposed device is the physical clearance of air flow through the atrophied or altered pharynx, causing in the first place snoring, then mild apnoea, up to the total obstruction and sudden death in the worst of cases.

To this end, the method of regulatable mandibular advancement is used by which the mandible is forced to be progressively moved forward, thereby pulling the tongue and the tissues that block posturally the pharynx. To this device features have been added allowing the opening of both jaws with a compensated advancement and unrestricted mandible movement with trajectory guided by a central bar and bilateral tracks.

Another change occurring in the human species has been dental overcrowding due to the progressive maxillar reduction, often preventing the correct position and interaction of contacts between teeth, causing interferences with consequent neurological, muscle, facial, neck, solar plexus and back disorders. Indirectly, the loss of teeth and their incorrect replacement causes prematurities and poor contacts.

The nerve endings connected to the TMJ (temporomandibular joint), if inadequate, eventually impinge on muscle nerve endings, potentially generating so-called "projected pain".

More recent studies place interferences in mandibular closure at the base of neurofocal dentistry and associate them to the cause of many systemic diseases, affecting different body parts in different individuals, which complicates diagnosis and its consequent treatment.

The second objective of the device disclosed is to unblock said interferences and provide a tool for the treatment of muscle and systemic disorders caused by interferences between maxillas and the occlusal surfaces being treated, which can be one of the causes of central apnoea.

The treatment of clearing the air flow through the pharynx by the method of mandibular advancement is abundantly documented, and the devices and construction forms of the maxillar plates supporting them have been described in detail and demonstrated.

The devices for dental, maxillar, muscle and joint protection by excitation of interferences, opening the vertical dimension and separating maxillas by use of sliding planes, have also been abundantly detailed and described.

The device proposed in the present invention is of the type constructed with splints on both arches joined by a mechanical device allowing the mandibular advancement, with an abundance of mechanisms and shapes described providing said advancement in one or another way. The differential factors of this device are its structural design and multipurpose use, and the Applicant is not aware of any other device having, for a same purpose, similar technical, structural and constituent features.

DESCRIPTION OF THE INVENTION

Thus, the intraoral regulatable mandibular advancement device applicable to preventing snoring and sleep apnoea that is proposed by the invention is a remarkable novelty within its field of application because, as shown when implemented, and in a non-limiting way, the above indicated objectives are achieved, its characteristic details, which make it unique, being adequately comprised in the final claims attached to the present descriptive memory.

The present invention provides a intra-oral regulatable mandibular advancement device, of the type used to join splints or light-weight plates adapted to the maxillas of the patient. The mechanical device can be made of medical steel or titanium, both following norm ISO 5832; nowadays or in the future with any biocompatible material that is resistant to the mechanical forces generated or demanded by the treatment.

The device for joining the maxillar plates is formed of an endless screw and two cross bars of diameter and curvature that are adequate to the device that will be fixed to the maxillar plates.

The endless screw is inside a sheath finished at the top with a crossing ring retaining a bar fixed to the upper plate. On the lower part of the device it has a crossing ring retaining the bar blocked by the lower plate and that moves from back to front inducing the mandibular advancement using the top blocked bar as support. Activation of the advancement is done via the screw head, for example of the pentalobular Torx® type, although any other form of screw can be used, which is exposed at the front of the device and is activated by using a special screwdriver for the device. The path, on the device, of the lower ring is sufficient for prolonging the natural mandibular advancement and for forcing a maximal advancement that is 60 to 90% of the physiological propulsion detected by the patient.

The plates giving support to the action of the device are, on their external occlusal face, of a rigid material that reproduces the correct plane for each patient, its vertical dimension and its lateral displacement. In addition, on the inside they contain a soft thermoadaptable or injectable material that moulds gently to the maxillary topography.

The objective of the soft material is to provide maximal comfort for the patient, especially in cases of gums of not great thickness over bone, or with teeth suffering periodontal disease, in which removal of the plates could lead to extraction of the periodontal teeth.

The plates made on natural teeth are of the same design and follow the same work protocol than those made for patients wearing fixed protheses or protheses over screwed-on or cemented implants.

The plates for patients carrying a prothesis over removable implants will be made on the components intended for the retention integrated in the plates of the device, the protheses being replaced at night by the patient for the device.

The plates for totally edentulous patients are prepared following the principles of the functional adhesive prothesis formulated by Dr. Schreinemaker, or any tested system that binds the maxillary plates of the device with sufficient retention for them to do their function.

Integrated in the upper and lower plates adapted to the patient are the pre-formed bars of the device, one or both, preferably the upper plate, being sufficiently recessed to allow the introduction of the device in the bars, once polished.

The differentiating factors of the device compared to any other mandibular advancement device are the following:

After analysing the multiple options in the state of the art relating to the problem of pharynx obstruction and occlusal interferences, the new design of the device allows immediate relief of the symptoms and initiates the principle triggering the solution to the problem in a non-aggressive approach.

Glossectomy or orthognatic surgery are more traumatic solutions and not all patients are ready to submit to them. The compressed air injection devices for nasal administration are uncomfortable, annoying and antisocial, and are only warranted in terminal cases of obstructive apnoea, and are considered useful primarily for this treatment.

The device proposed by the invention is designed for providing an effective solution to snoring and to a mild or moderate diagnosis of obstructive apnoea, favouring the elimination of neuropathological causes of central apnoea through neural unblocking, and consequently can also relieve cases of mixed apnoea.

In more detail, the following advantages are identified:

The unit size of the device is very small. It consists of a single central screw that can be placed in the space necessary for opening the device and in central position behind the central incisives, for elevating the vertical dimension between arches, a process necessary for de-programming the orthognatic system.

The opening of the device on a hinge axis situated anteriorly in front of the axis of the TMJ favours mandibular advancement, unobstructing the pharynx the more the mouth is opened by the patient, by forcing a greater mandibular advancement. A unique effect when compared to other devices.

This property of opening with advancement favours that the patient can maintain a closed mouth, but also allowing to have short conversations or the intake of fluids during the night.

Lateral displacements of the maxillas, favoured by the predetermined cancellation of preformed maxillary bars and by the specific design, preventing the stick-slip effect thanks to the conical and ellipsoidal shapes of the guiding rings for the bars integrated on the device. In this way, the patient adapts her/his mandible to the cushion or support on which it rests, enabling lateral movements without blocks and avoiding the claustrophobic effect of other devices.

It has sliding tracks that have a de-programming effect on the TMJ, allowing muscle relaxation of the patient and the omission of neuroblocking signals that favour systemic diseases and undefined neurofocal effects.

It is an all-in-one solution to diverse problems, from mild snoring and apnoea to occlusal pathology, which in some cases are inter-connected, while in others, snoring and stress can be solved simultaneously.

In the case of a diagnosis of functional malposition of teeth, the callibrated bars of the device can be applied to the corrective maxillary devices.

In patients undertaking a whitening treatment, the maxillary plates can be prepared for use as whitening trays that allow the housing of the low-intensity whitening liquids and pastes.

Although moving away from the objectives of the device, their combined used avoids the incompatible use of the same oral space for different treatments and the device can be installed with them. It is useful, for example, for the treatment of young patients, who are unsure about the severity of their ailment or reluctant about using the device regularly if there is no aesthetic compensation.

The laboratory work method for making the proposed device is the following:

The casts are prepared for manufacturing the vacuum plates.

The upper and lower plates are made in a vacuum or pressure machine.

Once cooled, the plate is cut, in the same way as an unload splint would.

The cast is articulated on the construction bite in a simple hinge or joint articulator.

The process is started on the lower maxilla, providing the plane of the upper maxilla.

The plate manufactured is set on the cast, sealing the margins with wax so that the acrylic material does not exceed the limits.

A special adhesive acting as plastic-resin bonding agent is spread onto the rigid part. After drying, the acrylic material is added by the usual orthodontic method, creating a ideal equilibrium plane with an approximate height thickness of 1.3 mm and between canines and second molars.—During the contouring, scalloped necks are left on plaque.

To make the upper plate, the VD (vertical dimension) is increased to create sufficient space for the device.

The lower plate is prepared by adding plastic adhesive forming a ribbon to separate the resins, to the lower planes of occlusal surfaces in order to create a guide plane for the upper plate.

The margins of the plate are sealed with wax as with the lower plate.

The acrylic material is added to the upper maxilla, only creating tracks from canines to molars.

Once the resin has been added, the upper plate is articulated to the lower plate, checking that the upper and lower planes slide properly.

Contouring is done following the same procedure used for the lower plate.

Once both plates have been contoured, the lower cast is prepared by inserting the lower 1.5 mm bar, which will serve as a lateral displacement guide for the orthoapnoea device.

Only in special cases, use a totally round bar for the lower plate, which does not have a removal region on upper and lower plates.

The free path of the bar for the device is from canine to canine. The bar should be installed considering the height of the device and according to the advancement register made at the clinic, in such a way that it coincides ideally with the ideal placing on the upper plate.

Once the device is blocked on the lower maxilla, the bar is marked and positioned on the upper cast, leaving the bar ready for its mounting.

The upper bar, of specific annulation and dimensions, is the one with a removal region for the device.

The plate must be prepared leaving a free path for the bar in the region between canines for the movement of the device.

Both bars and sliding surfaces should be balanced and on the same plane, highering the whole above the minimal VD, unless the clinician indicates otherwise.

When preparing special plates, such as orthodontic plates, after forced extrusion, with whitening, over removable implants with a removable prothesis, or on edentulous patients and other possibilities, follow the process more appropriate for each speciality.

In view of the above, the described regulatable intraoral mandibular advancement device that can be used to prevent snoring and sleep apnoea is therefore an innovative structure with hitherto unknown structural and constitutional features for said purpose. These qualities, together with its practical usefulness, provide a sufficient basis for obtaining the privilege of exclusivity applied for.

DESCRIPTION OF THE DRAWINGS

For a better understanding of the invention, an embodiment of the object of the invention is shown by way of a non limiting example in the accompanying drawings, according to the claims, attached to the present descriptive memory.

In said drawings.

DESCRIPTION OF AN EMBODIMENT EXAMPLE OF THE INVENTION

Figure 1:
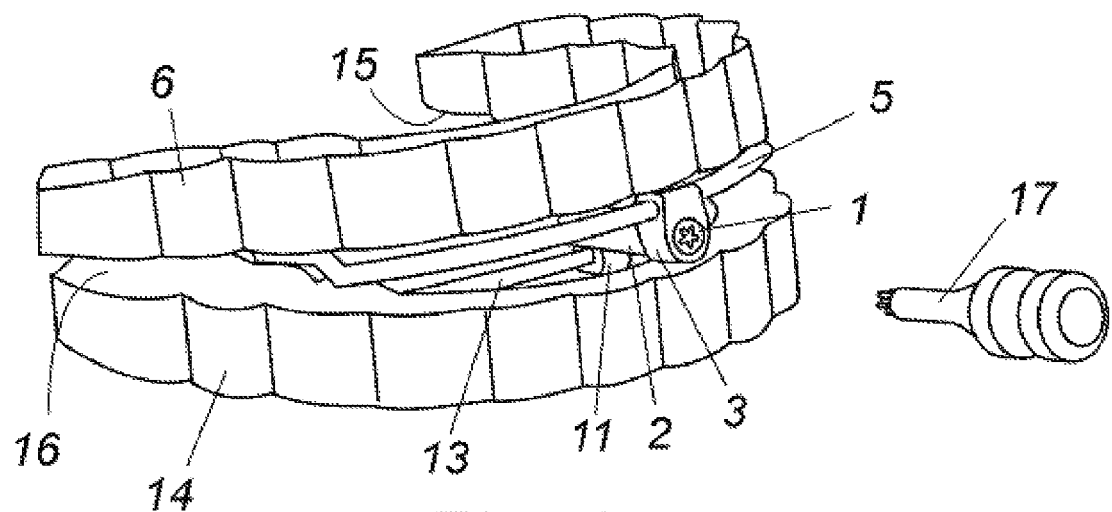
FIGS. 1 and 2. They show perspective, front and back views, respectively, of the regulatable intra-oral mandibular advancement device that is object of the invention, showing the main parts and elements it comprises, as well as the configuration and arrangement thereof.
Figure 2:
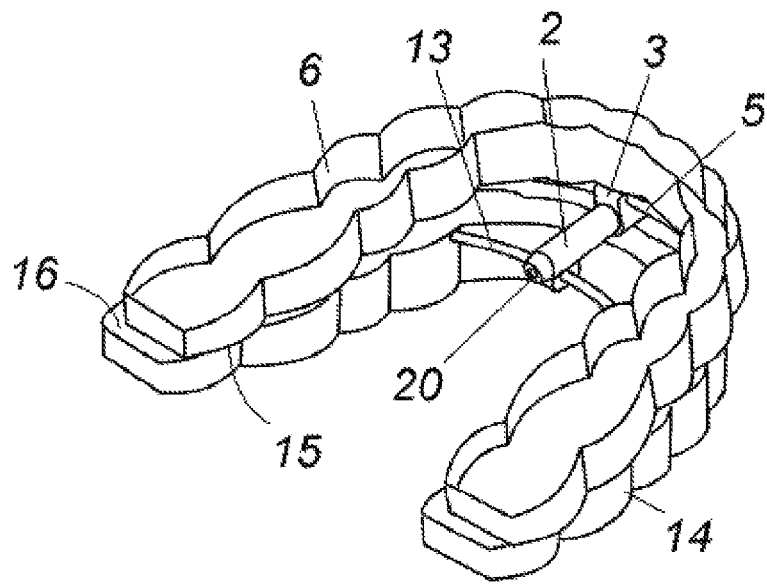
Figure 3:
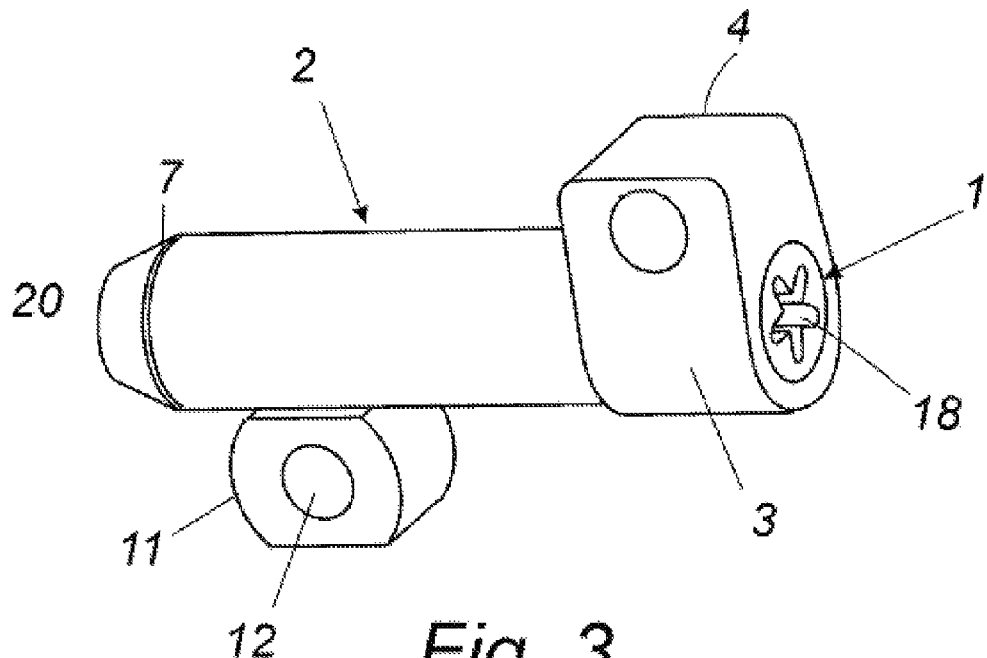
FIGS. 3 and 4. They show perspective views of the screw and sheath housing it, which constitute the displacement mechanism allowing the advancement of the mandibular plate with respect to the maxillary plate; mounted and exploded views, respectively.
Figure 4:
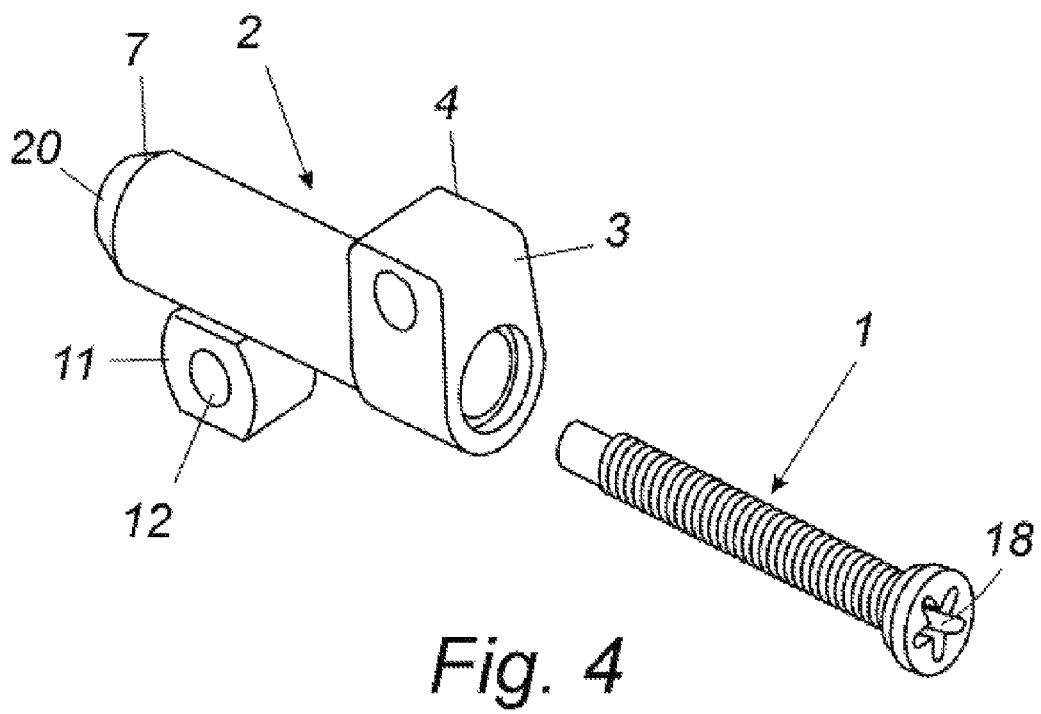
Figure 5:
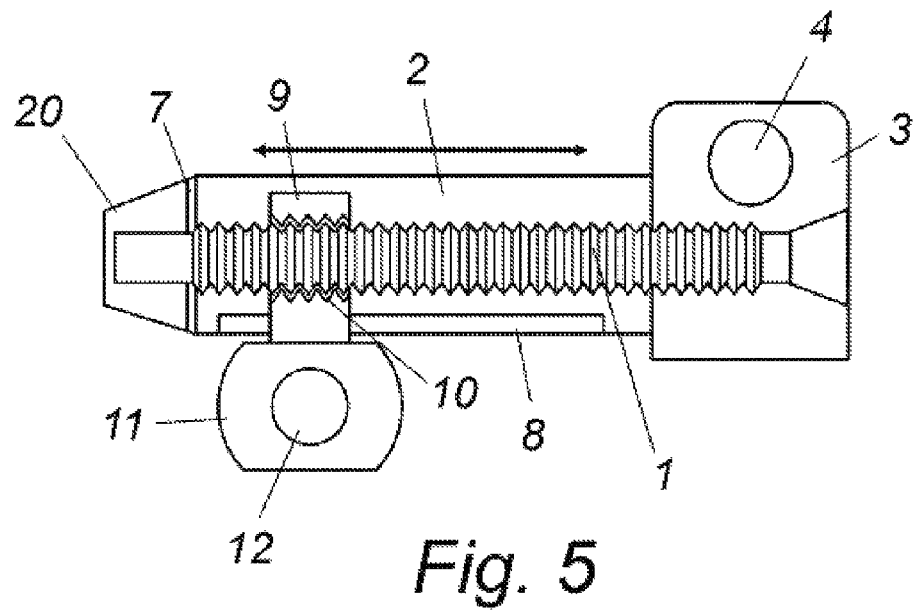
FIG. 5. It shows a cross-section view, according to a longitudinal section, of the mechanism shown in FIGS. 3 and 4.
Figure 6:
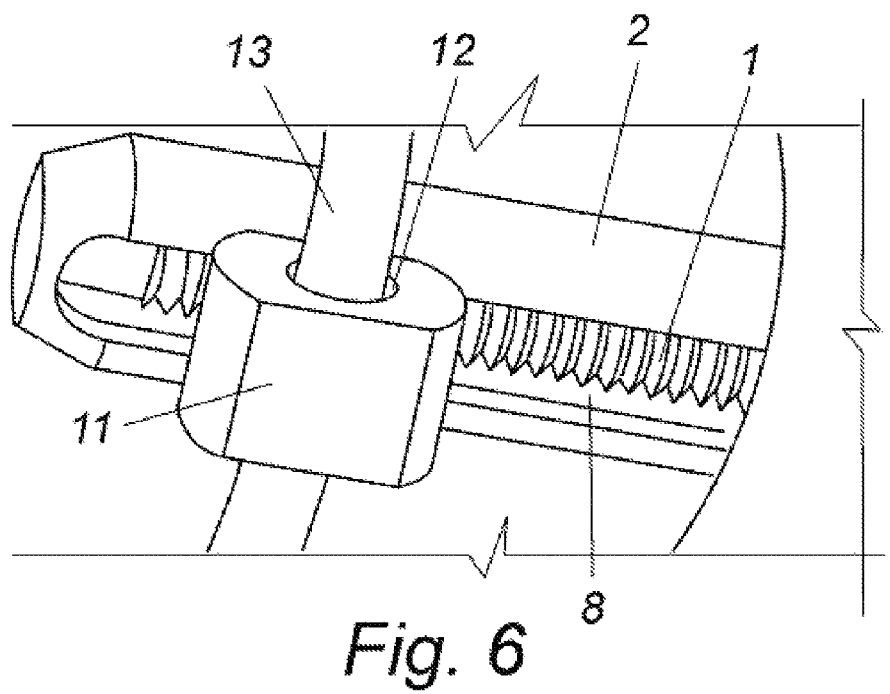
FIG. 6. It shows a detail of the lower part of the displacement mechanism coupled to the bar of the lower plate, showing the longitudinal groove enabling the course of the lower displacement ring.

In view of the discussed figures and according to the numbering adopted, a preferred embodiment example of the invention can be seen, comprising the parts and elements described in detail below.

Thus, as can be seen in said figures, the device of the invention is of the type comprising two maxillary plates, a lower or mandibular plate (16) and an upper plate (6), connected by a displacement mechanism that allows to regulate their mutual positions thereby enabling the mandibular advancement in the patient, consisting of a screw (1) housed in a polygonal cylindrical sheath (2) that has, on its front region, an upper displacement ring (3), open or closed and narrowing at the centre, which serves as guiding housing (4) for an upper bar (5) fixed to the upper maxillary plate (6).

Said screw (1) is fixed to the sheath (2) by a washer (7) by radial riveting (20), laser welding or with a nut, on its rear part, and, on its lower part, the sheath (2) has a longitudinal groove (8) enabling the course of an inner mobile ring (9) having a thread (10), connecting and being displaced by the screw (1), and on which a lower displacement ring (11) is arranged, open or closed, said ring being provided with a perpendicular hole (12) with elipsoidal conicity, in which the lower bar (13) fixed to the lower maxillary plate (14) is inserted.

Thus, the upper (3) and lower (11) rings are prepared for giving mobility to the device on the bars (5 and 13) inserted in upper and lower plates (6 and 14), which have, respectively, opposing sliding planes (15 and 16).

The movement of advancement of the lower maxilla is activated by operating a screwdriver (17), designed to fit a socket (18), for example of the pentalobular Torx® type, of the screw (1), and turning clockwise, moving the lower ring (11) on the screw (1) down the course of the longitudinal groove (8), which advances the lower bar (13), which is fixed to the lower maxillary plate (14), while remaining in the selected position.

It is noteworthy that the displacement mechanism has small dimensions, approximately 15 mm in length and a frontal height of 6.5 mm, allowing by virtue of its small size its insertion in central position between the maxillas.

On the other hand, the upper (3) and lower (11) displacement rings have been specifically designed to avoid the effect technically defined as "stick-slip", or blocking/unblocking of bars (5 and 13) during their course.

The bars (5 and 13) are preformed in their central part with a radial annulation of 14 to 20 degrees and show a longitudinal grooving that coincides with the dimensions of the upper ring (3) when open for the dismounting of the plate.

When opening the mouth, the device acts with a front hinge axis opposed to the TMJ axis, inducing a greater advancement of the mandible (19) by virtue of the special arrangement of the upper (3) and lower (11) rings, enabling the course forward of the lower ring (11) fixed to the lower bar (13) inserted in the maxillary plate.

The retentive upper (6) and lower (14) maxillary plates have sliding platforms based on the state-of-the-art miorelaxant plates with opposing sliding planes (15 and 16).

It is noteworthy that the bars (5, 13), the sliding mechanism coupled to them, which consists of a screw (1) and a sheath (2), as well as the sliding planes (15, 16) of the maxillary plates are adequate for mounting on corrective plates for dental positioning, or orthodontic plates, thus having the joint effect of mandibular advancement and orthodontics, as well as on patients with prothesis on removable implants, using the same anchors than those used by the protheses adapted to the maxillary plates (6 and 14).

For mounting on certain totally edentulous patients, the state-of-the-art principles given by Dr. Schreinemaker, and similar or excellent adhesive systems are applied in a strict manner.

It is also noted that the bars (5, 13), the sliding mechanism of screw (1) and sheath (2), and the sliding plates (15, 16) can be manufactured using a CAD-CAM milling system for plastic or by stereolithography, or by using a muffle furnace, or by pouring or by matting of powder on liquid, or by injection of a plastic charge or by using any system available in the state-of-the-art that can be used to make plates adapted and customized to the patient's maxilla.

Similarly, the proposed device includes indications that are marked on the basal milled surface, which serve as a positional reference to reposition the device during dismounting or repair operations.

Lastly, the plates (6 and 14) giving support to the action of the device on the external and occlusal part thereof are of a rigid material that recreates the plane specifically appropriate for each patient, both its vertical dimension and lateral displacement. On the internal part they contain a thermoadaptable or injectable soft material that moulds gently onto the maxillary topography.

Having described sufficiently the nature of the present invention, as well as the manner for putting it into practice, it is considered unnecessary to provide further detail for anyone skilled in the art to understand its scope and any advantages derived therefrom, expressly stating that it can be essentially put into practice in other embodiments differing in detail from that given by way of example, and which are also comprised within the scope of protection claimed as long as the fundamental principle is not altered, changed or modified.

The invention claimed is:

1. Intraoral regulatable mandibular advancement device, for preventing snoring and sleep apnoea, of the type used to join upper and lower maxillary plates adapted to conform the patient's maxillas and intended for prosthetic tasks in the field of odontology, whose purpose is to advance the mandible to avoid the obstruction of air flow through airways, the advancement device comprising: a screw housed in a polygonal cylindrical sheath that has on its front region an upper displacement ring which serves as a guiding house for an upper bar fixed to the upper maxillary plate, and wherein the sheath has a longitudinal groove for receiving an inner mobile ring having a thread connecting and being displaced by the screw, and on which a lower displacement ring is arranged said ring being provided with a perpendicular hole with ellipsoidal conicity that receives a lower bar that is fixed to the lower maxillary plate wherein said screw is blocked in the sheath in the rear part thereof and the upper and lower rings are prepared for giving mobility to the device on the upper and lower bars inserted in upper and lower plates, which have respectively opposing sliding planes.

2. Intraoral regulatable mandibular advancement device, for preventing snoring and sleep apnoea, according to claim 1, wherein a displacement mechanism is formed by the screw and the sheath, the screw and sheath each having small dimensions, approximately 15.5 mm in length and a frontal height of 6.5 mm, allowing by virtue of size their insertion in a central position between the maxillas.

3. Intraoral regulatable mandibular advancement device, for preventing snoring and sleep apnoea, according to claim 2, wherein the screw has a socket head suitable for a purpose-designed screwdriver.

4. Intraoral regulatable mandibular advancement device, for preventing snoring and sleep apnoea, according to claim 2, wherein the screw is retained in the polygonal cylindrical sheath directly or by a washer in a rear part thereof by radial riveting, laser welding or with a nut.

5. Intraoral regulatable mandibular advancement device, for preventing snoring and sleep apnoea, according to claim 1, wherein the upper and lower displacement rings have a specific design preventing blocking of the upper and lower bars during their course.

6. Intraoral regulatable mandibular advancement device, for preventing snoring and sleep apnoea, according to claim 5, wherein the upper and lower bars are preformed in their central part with a radial annulation of 14 to 20 degrees and show a longitudinal grooving coinciding with the dimensions of the upper ring open for dismounting of the plate.

7. Intraoral regulatable mandibular advancement device, for preventing snoring and sleep apnoea, according to claim 1, wherein the upper and lower maxillary plates have sliding platforms with opposing sliding planes.

8. Intraoral regulatable mandibular advancement device, for preventing snoring and sleep apnoea, according to claim 7, wherein the upper and lower bars, the sliding platforms coupled to them, and the sliding planes of the maxillary plates are adequate for mounting on corrective plates for dental positioning, or orthodontic plates, having the of mandibular advancement and orthodontics.

9. Intraoral regulatable mandibular advancement device, for preventing snoring and sleep apnoea, according to claim 7, wherein the upper and lower bars, the sliding platforms coupled to them, and the sliding planes of the maxillary plates, are adequate for mounting on patients with removable prosthesis on implants, using a same anchors as a prothesis adapted to mount the maxillary plates.

10. Intraoral regulatable mandibular advancement device, for preventing snoring and sleep apnoea, according to claim 7, wherein the upper and lower bars, the sliding platforms coupled to them, and the sliding planes of the maxillary plates are adequate for mounting on certain totally edentulous patients.

11. Intraoral regulatable mandibular advancement device, for preventing snoring and sleep apnoea, according to claim 1, wherein the upper and lower bars, the sliding platforms and the sliding planes can be manufactured using on of a CAD-CAM milling system for plastic or by stereolithography, or by using a muffle furnace, or by pouring or by matting of powder on liquid, or by injection of a plastic charge.

12. Intraoral regulatable mandibular advancement device, for preventing snoring and sleep apnoea, according to claim 1, wherein it incorporates markings on a basal milled surface which serve as a positional reference to reposition the device during dismounting or repair operations.

13. Intraoral regulatable mandibular advancement device, for preventing snoring and sleep apnoea, according to claim 1, wherein the upper and lower maxillary plates that support the action of the device, in its external and occlusal part, are made of a rigid material that creates the plane specifically appropriate for each patient, both its vertical dimension and lateral displacement, and in that, on the internal part, it contains a thermoadaptable or injectable soft material that is configured to molds gently onto the maxillary topography.

* * * * *